(12) United States Patent
Danielsen

(10) Patent No.: US 9,095,677 B2
(45) Date of Patent: Aug. 4, 2015

(54) SAFETY SYSTEM FOR A BREATHING APPARATUS FOR DELIVERING AN ANESTHETIC AGENT

(75) Inventor: Lars Danielsen, Hässelby (SE)

(73) Assignee: Maquet Critical Care AB, Solna (SE)

( * ) Notice: Subject to any disclaimer, the term of this patent is extended or adjusted under 35 U.S.C. 154(b) by 1136 days.

(21) Appl. No.: 12/664,414

(22) PCT Filed: Jun. 13, 2007

(86) PCT No.: PCT/EP2007/055833
§ 371 (c)(1),
(2), (4) Date: Jun. 16, 2010

(87) PCT Pub. No.: WO2008/151667
PCT Pub. Date: Dec. 18, 2008

(65) Prior Publication Data
US 2010/0269820 A1    Oct. 28, 2010

(51) Int. Cl.
*A61M 16/18* (2006.01)
*B67D 1/12* (2006.01)

(52) U.S. Cl.
CPC .......... *A61M 16/18* (2013.01); *A61M 16/183* (2013.01); *A61M 2205/14* (2013.01); *A61M 2205/18* (2013.01); *A61M 2205/3306* (2013.01); *A61M 2205/3331* (2013.01); *A61M 2205/3389* (2013.01); *A61M 2205/50* (2013.01); *A61M 2205/52* (2013.01); *A61M 2205/6018* (2013.01); *B67D 1/1247* (2013.01)

(58) Field of Classification Search
CPC ... A61M 16/18; A61M 16/183; B67D 1/1247

USPC .......... 128/200.19, 200.21, 200.23, 202.22, 128/203.12–203.14, 203.25, 128/204.21–204.22; 141/18, 95, 198
See application file for complete search history.

(56) References Cited

U.S. PATENT DOCUMENTS

| 3,665,209 | A | * | 5/1972  | Webb et al. ................... 307/118 |
|-----------|---|---|---------|-------------------------------------------|
| 4,345,612 | A | * | 8/1982  | Koni et al. ............... 137/101.19     |
| 4,441,027 | A | * | 4/1984  | Richardson et al. .......... 250/577       |
| 4,625,779 | A |   | 12/1986 | Ryschka et al.                             |
| 4,870,960 | A | * | 10/1989 | Hradek ..................... 128/202.22    |
| 5,157,968 | A | * | 10/1992 | Zfira ............................. 73/149 |
| 5,186,057 | A | * | 2/1993  | Everhart ..................... 73/861.41   |
| 5,197,462 | A | * | 3/1993  | Falb et al. ................ 128/203.14    |
| 5,243,973 | A | * | 9/1993  | Falb et al. ................ 128/203.27    |
| 5,470,511 | A | * | 11/1995 | Laybourne et al. ............ 261/55       |
| 5,505,236 | A | * | 4/1996  | Grabenkort et al. .......... 141/329       |

(Continued)

FOREIGN PATENT DOCUMENTS

WO    WO 00/27458    5/2000
WO    WO 2007/006348    1/2007

*Primary Examiner* — Justine Yu
*Assistant Examiner* — Christopher Miller
(74) *Attorney, Agent, or Firm* — Schiff Hardin LLP

(57) ABSTRACT

A safety system for a breathing apparatus for delivery of an anesthetic agent having an anesthetic agent vaporizer having a reservoir for containing a liquid anesthetic agent has a reservoir for containing a liquid medical agent, a port for filling the reservoir with the liquid anesthetic agent, and a sensor device for sensing a filling action of the port. A change of position of a lid covering the port can be detected, or insertion of a fill vessel into the port can be detected. Thus safety of the equipment is improved by being able to depressurize the reservoir before opening a filling valve for communication of the port with the interior of the reservoir.

17 Claims, 5 Drawing Sheets

(56) References Cited

U.S. PATENT DOCUMENTS

| | | | |
|---|---|---|---|
| 5,522,378 A * | 6/1996 | Ritson et al. | 128/200.14 |
| 5,572,992 A * | 11/1996 | Kankkunen et al. | 128/203.14 |
| 5,621,392 A * | 4/1997 | Paolini et al. | 340/603 |
| 5,810,001 A * | 9/1998 | Genga et al. | 128/202.27 |
| 5,824,885 A * | 10/1998 | Lekholm | 73/53.01 |
| 6,138,672 A * | 10/2000 | Kankkunen | 128/203.12 |
| 6,289,891 B1 * | 9/2001 | Cewers | 128/203.12 |
| 6,626,862 B1 * | 9/2003 | Duchon et al. | 604/110 |
| 6,745,800 B1 * | 6/2004 | Sansom | 141/198 |
| 6,878,133 B2 | 4/2005 | Ahlmen et al. | |
| 7,730,885 B2 * | 6/2010 | Gippert et al. | 128/203.12 |
| 7,997,268 B1 * | 8/2011 | Leonard et al. | 128/203.12 |
| 2002/0069876 A1 * | 6/2002 | Loser et al. | 128/203.19 |
| 2002/0157670 A1 * | 10/2002 | Kullik et al. | 128/203.12 |
| 2004/0070408 A1 * | 4/2004 | Florin et al. | 324/662 |
| 2005/0072421 A1 * | 4/2005 | Suman et al. | 128/200.23 |
| 2005/0076904 A1 * | 4/2005 | Jones et al. | 128/200.23 |
| 2006/0232791 A1 * | 10/2006 | Turrini | 356/621 |
| 2007/0102923 A1 | 5/2007 | Niemela | |

* cited by examiner

US 9,095,677 B2

SAFETY SYSTEM FOR A BREATHING APPARATUS FOR DELIVERING AN ANESTHETIC AGENT

FIELD OF THE INVENTION

This invention pertains to the field of systems for increasing the safety of a breathing apparatus for delivery of an anesthetic agent. More specifically, the invention relates to a system for increasing the safety in connection with refilling a liquid anesthetic agent delivery equipment with a liquid anesthetic agent.

DESCRIPTION OF THE PRIOR ART

A pressurized liquid anesthetic agent delivery equipment is disclosed in U.S. Pat. No. 6,878,133. The equipment includes a primary reservoir for receiving the medical liquid to be delivered, and a secondary reservoir, fluidly connected to the primary reservoir. When the equipment is to be replenished with liquid anesthetic agent, the secondary reservoir is disconnected from the primary reservoir and the secondary reservoir is operative for providing the medical fluid to the patient during refilling of the primary reservoir with liquid anesthetic agent. When the primary reservoir is disconnected from the secondary reservoir, a driving pressure originally present in the primary reservoir is first equilibrated to the atmospheric pressure, whereupon a liquid anesthetic agent source is connected to the primary reservoir and emptied into the primary reservoir. When the primary reservoir is sufficiently refilled, the liquid source is removed, and the driving pressure is restored in the primary reservoir. Then the primary reservoir is reconnected to the secondary reservoir for continued operation.

Another similar equipment is disclosed in WO 2007/006348 of the same applicant as the present application.

Such equipment would work well were it not for the human factor.

In order to adjust the equipment for refilling, the operator switches one or several valves in order to equilibrate the primary reservoir. In a typical clinical operating environment of such liquid anesthetic agent delivery equipment, the operator may unintentionally loose the attention of the equipment. This might lead to less desired effects. For instance, when the primary reservoir is about to be replenished with fresh liquid anesthetic agent. In case and the primary reservoir is not equilibrated to atmospheric pressure, i.e. still under pressure, before establishing fluid contact through the refill port between the primary reservoir and the medical liquid source, e.g. a bottle with liquid anesthetic agent, the medical liquid might escape into the surrounding environment. In extreme cases, the medical liquid may squirt or eject from the reservoir or the medical liquid source due to the overpressure thus present in the reservoir and communicated through the refill port. Inhalation of vaporized anesthetic agent by healthcare personnel in the surrounding environment can cause drowsiness and may cause other health troubles when one is exposed to the anesthetic agent. Furthermore, certain volatile medical liquids might be flammable at atmospheric pressure.

Thus, there is a need in the art to reduce the human factor influence during refilling of a medical liquid into a medical liquid delivery equipment.

Hence, an improved medical liquid delivery equipment would be advantageous and in particular allowing for increased patient safety and/or operator safety.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a safety system according to the appended patent claims.

A safety system for a medical equipment has a reservoir for containing a liquid medical agent, a port for filling the reservoir with the liquid medical agent, and a sensor device for sensing a filling action at the port. For instance a change of position of a lid covering the port is detected, or insertion of a fill vessel into the port is detected. Thus safety of the equipment is improved, for instance by being able to depressurize the reservoir before opening a filling valve for communication of the port with the inner of the reservoir.

According to a first aspect of the invention, a safety system for a breathing apparatus for delivery of an anesthetic agent having an anesthetic vaporizer is provided that has a reservoir for containing the anesthetic agent in liquid form, and a port for filling the reservoir with the liquid anesthetic agent, wherein the apparatus has a sensor device for sensing a filling action of the port.

In an embodiment the safety system may be configured to arrange the breathing apparatus for delivery of an anesthetic agent having an anesthetic vaporizer into a filling condition in dependence of a signal of the sensor device sensing the filling action of the port.

In an embodiment the reservoir may be adapted to be pressurized for delivery of the anesthetic agent, and wherein the anesthetic agent vaporizer is an anesthetic vaporizer for pressurized anesthetic agents.

In an embodiment the control device is arranged to relieve an over-pressure prevailing in the reservoir before filling in order to arrange the breathing apparatus for delivery of an anesthetic agent having an anesthetic vaporizer into the filling condition.

In an embodiment, the sensing device may be arranged for sensing when a protection member is positioned in its home position and to emit a signal when the protection member is in the home position. Alternatively, the sensing device may be arranged for sensing when the protection member is positioned in a position, in which the port is open and free to receive a filling means, and to emit a signal when the protection member is in the opened position. The protection member may be a lid, which may be moveable in a linear, rotational or pivoting movement.

In another embodiment, the sensor device may operate by means of electromagnetic radiation, such as ultraviolet, visible or infrared light. In a further embodiment, the sensor may operate mechanically, capacitively, thermally, pneumatically or hydraulically.

In a still further embodiment, the sensor may emit an electric signal, which is transmitted to a control device, which is operative to put the equipment in the filling condition. The control device may be arranged to relieve an over-pressure prevailing in the reservoir before filling.

In a yet further embodiment, the control device may be arranged to emit a warning signal if the filling condition or the filling action prevails for more than a predetermined time period. Moreover, the control device may be arranged to terminate the filling condition if the filling condition or the filling action prevails for more than a predetermined time period.

In still a further embodiment the system may alternatively or additionally have a second sensor device arranged adjacent the port for sensing when a filling vessel is inserted in the port, and thus for detecting a filling action of the port. The second sensor device may be a sensor arranged at one side of the port and a detector arranged at an opposite side of the port. The sensor may be arranged to emit a signal until a fill vessel adapter is inserted in the port. Alternatively, a fill vessel insertable into the port may comprise a sensor detectable unit for detection by the second sensor device upon insertion of the fill vessel into the port.

According to a further aspect of the invention, a method is provided for providing safety for a breathing apparatus for delivery of an anesthetic agent having an anesthetic agent vaporizer comprising a reservoir for containing a liquid anesthetic agent and a port for filling the reservoir with the liquid anesthetic agent, and a sensor device, wherein he method comprises sensing a filling action of the port with the sensor device.

In an embodiment the method may comprise arranging the breathing apparatus for delivery of an anesthetic agent having an anesthetic agent vaporizer into a filling condition upon sensing the filling action of the port.

According to a yet further aspect of the invention, a computer program is provided for providing safety for a breathing apparatus for delivery of an anesthetic agent having an anesthetic agent vaporizer comprising a reservoir for containing a liquid anesthetic agent and a port for filling the reservoir with the liquid anesthetic agent, and a sensor device, wherein the computer program for processing by a computer comprises a code segment for sensing a filling action of the port with the sensor device.

According to another aspect of the invention, a signal for providing safety for a breathing apparatus for delivery of an anesthetic agent having an anesthetic agent vaporizer comprising a reservoir for containing a liquid anesthetic agent and a port for filling the reservoir, the signal being generated by a sensor device for sensing a filling action of the port, the signal enabling arranging the breathing apparatus for delivery of an anesthetic agent having an anesthetic agent vaporizer into a filling condition.

Further embodiments of the invention are defined in the dependent claims.

Some embodiments of the invention provide for increased patient safety by providing safely continuous delivery of a medical agent even at periods of refilling an anesthetic agent vaporizer, comprised in a breathing apparatus for delivery of an anesthetic agent, from which the anesthetic agent is delivered to the patient, e.g. by vaporizing the liquid anesthetic agent and adding it to breathing gases, for instance by injecting the liquid anesthetic agent into a flow of breathing gas.

Some embodiments of the invention also provide for reduced possibility of incidents during refilling the anesthetic agent vaporizer, comprised in a breathing apparatus for delivery of anesthetic agents.

Some embodiments provide for increased operational safety of a vaporizer having a pressurized receptacle for a liquid anesthetic agent, by ensuring a non-pressurized state of the receptacle containing the liquid anesthetic agent during a filling action of the receptacle with liquid anesthetic agent. The filling action may comprise filling or refilling the receptacle.

Some embodiments of the invention also provide for reduced possibility of contaminating the medical agent comprised in the breathing apparatus for delivery of an anesthetic agent.

DESCRIPTION OF THE PREFERRED EMBODIMENTS

Figure 1:
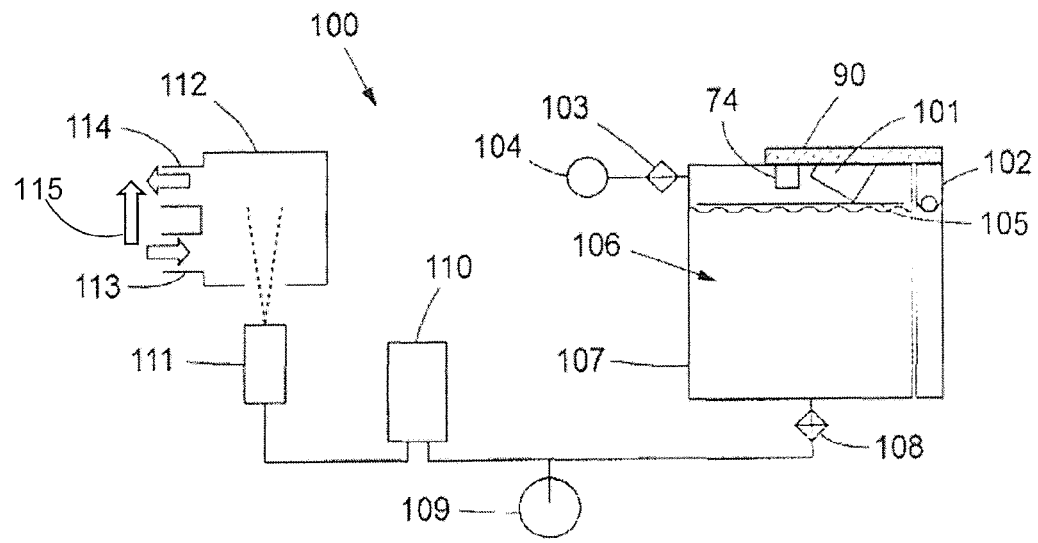
FIG. 1 is a schematic block diagram of an anesthetic vaporizer representing an embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to an anesthetic vaporizer. However, it will be appreciated that the invention is not limited to this application but may be applied to many other medical liquid delivery systems.

FIG. 1 is a schematic block diagram of an anesthetic vaporizer 100 in an embodiment of the present invention. In use the anesthetic vaporizer is a component of a breathing apparatus for delivery of anesthetic agents. The anesthetic vaporizer 100 has a receptacle 107 for receiving a liquid anesthetic agent 106 via filling valve 101. A level sensor 102 measures a current filling level of the receptacle 107 with liquid. A float 105 prevents the pressurized liquid anesthetic agent 106 from becoming saturated with gas. Via a filter 103 and a pressure sensor 104 the pressure inside the receptacle may be measured. The liquid anesthetic agent 106 may be transported, when the receptacle 107 is pressurized, via a filter 108, and a safety valve 109 from the receptacle 107 to an injector valve 111 into a chamber 112. A further pressure sensor 110 is provided in the line connecting the receptacle 107 with the injector valve 111. The chamber 112 receives a flow of gas via an input port 113. The flow of gas thus may be provided with a varying degree of vaporized anesthetic agent and leave the anesthetic vaporizer via an exit port 114.

A protecting member, here in form of a lid 90, is provided covering the entry port to the filling valve 101. A sensor is provided for detecting the position of the lid 90 relative the entry port 101.

Figure 2:
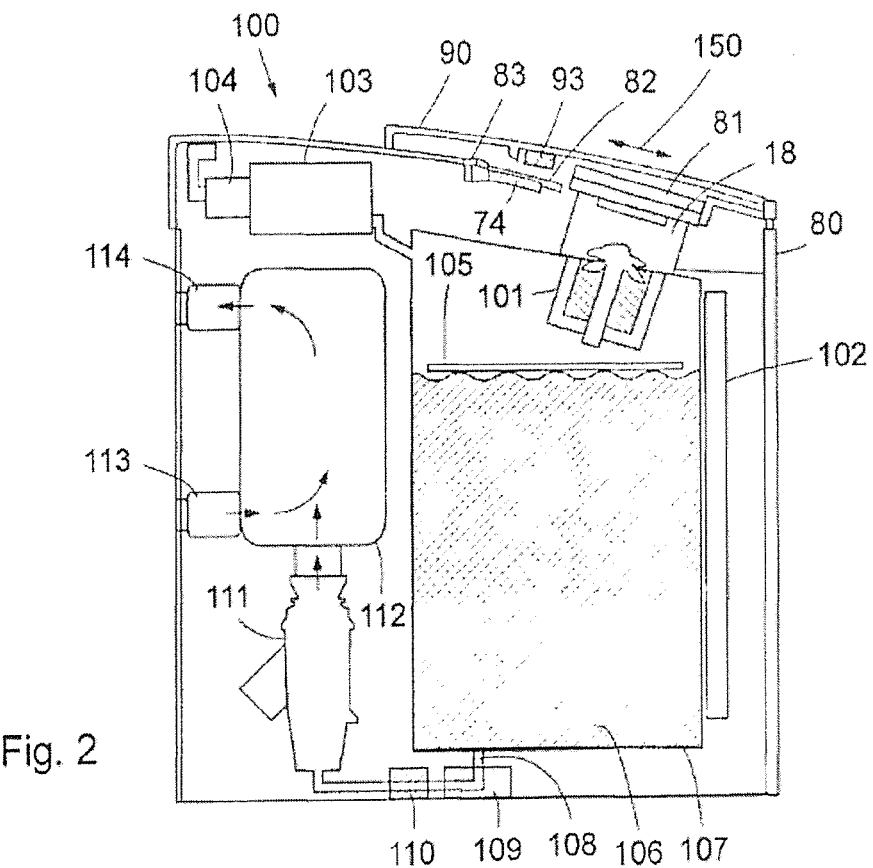
FIG. 2 is a sectional view in vertical plane II of an anesthetic vaporizer having a safety system according to an embodiment of the invention.

FIG. 2 is a sectional view in vertical plane II of an anesthetic vaporizer corresponding to the vaporizer schematically shown in FIG. 1. Vertical plane II is shown in the schematic view of the top of the vaporizer in the upper part of FIG. 2, wherein the opening 81 is shown for orientation. The receptacle 107 is provided with a refill port 18, which can be of the type disclosed in WO 2005/056093 of the same applicant as the present application, the technical contents of which is incorporated in its entirety in the present specification by reference. Alternatively to the illustrated and described filling port 18, other units, assemblies or arrangements devised for refilling an anesthetic vaporizer with liquid anesthetic agent from a container, which are known to the skilled person, may be implemented in other embodiments.

Basically, this refill port 18 has a filling assembly arranged in the refill port 18 and a valve system having a filling valve 101. A container, such as bottle, containing a medical liquid is provided with an adapter fitting in the refill port 18. When the bottle with the adapter is inserted in the refill port, the valve system is opened. Then, a further valve system in the adapter is opened and a fluid path is formed for permitting communication with the inner of receptacle 107. The liquid thus is allowed to flow to the inner of the receptacle 107, replacing the liquid in the container with gas from the inner of receptacle 107.

A mentioned above, it is important that the receptacle 107 is not pressurized during this refill procedure.

In order to protect the port 18 from being contaminated by dust and debris during use, the port 18 is normally closed by a protecting member, in the embodiment shown in FIG. 1 in the form of lid 90 that covers the opening 81 of the port 18. Such a protecting member can be of any suitable type, for example a screw cap for closing the port 18 in a gas-tight manner. In embodiments the protecting member may be a wall closing the entrance to the port 18 without sealing it in a gas-tight manner. The protecting member also prevents unintended operation of the port and the valve system in the port.

The protecting member is removable or displaceable in order to expose the port 18. The protecting member may be rotatable around a shaft. Alternatively or additionally, the protecting member may be linearly displaceable as shown in FIG. 2 by arrow 150, which shows the port 18 provided with a lid 90. The lid 90 is arranged in a groove 71 of the anesthetic vaporizer. The lid 90 is, by means of a handle 72, moveable between a first position, shown in solid lines and closing the entrance of port 18, and a second position shown in broken lines and exposing the opening 18 so that a bottle can be inserted in the port.

The lid 90 is provided with an indication in the form of a reflecting plate 93 arranged on the inner thereof. A sensor 74, for example in the form of a reading fork having a light source and a detector, is arranged in a position opposite to a reflecting plate when the lid 90 is in its closed position, as shown in FIG. 2.

When the reflecting plate 93 is positioned opposite to the sensor 74, the light from the light source, such as a light emitting diode LED, is reflected by the reflecting plate 93 toward the detector, which generates an output signal. This output signal may be provided to a control device.

The function of a control device, or a separate control circuit e.g. of an anesthesia machine in which the vaporizer 100 is installed, is now described in more detail. The control device may have a control program, which upon receipt of a signal from the sensor 74 performs one or several of the following operations. As the sensor 74 indicates that the port 18 is at least partly covered by the lid 90 when a reflection based signal is received, the receptacle 107 may be pressurized and anesthetic agent may be delivered therefrom.

In this case, the lid 90 is displaced transversally in order to reveal (expose) the port 18, whereupon sensor 74 no longer detects the reflection signal, thus indicating a filling action to the control unit. In this case the filling action is indicated by opening the lid 90 and detecting that the lid 90 is opened. Upon detecting the filling action, the receptacle 107 is now automatically de-pressurized via a suitable valve, e.g. until the pressure sensor 104 indicates that atmospheric pressure is present in the inner of receptacle 107. The anesthetic vaporizer is now in a filling condition.

In other embodiments the filling condition of an anesthetic vaporizer may be accomplished in other ways than de-pressurizing the anesthetic vaporizer. For instance, during operation of the anesthetic breathing apparatus, metering from the anesthetic vaporizer may be interrupted, e.g. by suitable electronic or mechanical switching action of the anesthetic vaporizer. The anesthetic vaporizer may be taken completely or at least partly out of operation for establishing a filling condition thereof. For instance a gas flow through the vaporizer may be stopped, decreased, or diverted into other suitable channels in the anesthetic breathing apparatus. Alternatively or in addition, and depending on the design of the anesthetic vaporizer and the anesthetic breathing apparatus, a fresh gas flow through the anesthetic vaporizer may be stopped or decreased, or a bypass of the fresh gas flow passing the vaporizer towards a breathing circle may be activated.

When the anesthetic vaporizer is in a filling condition, anesthetic agent may be replenished via port 18 and filling valve 101 without possibility of spillage by inserting a filling container into port 18.

When the bottle is removed and the lid 90 is returned to its closed position, the signal of sensor 74 re-appears. Thus the filling action is terminated and an indication of a filling action by the sensor ceases. Then, the control device can be arranged to allow pressurization of receptacle 107 in order to place the equipment in an operating condition, after being refilled.

The lid 90 may be arranged to be moved aside when the bottle provided with the adapter is inserted into the port 18, for example by means of a cam surface (not shown).

Figure 3:
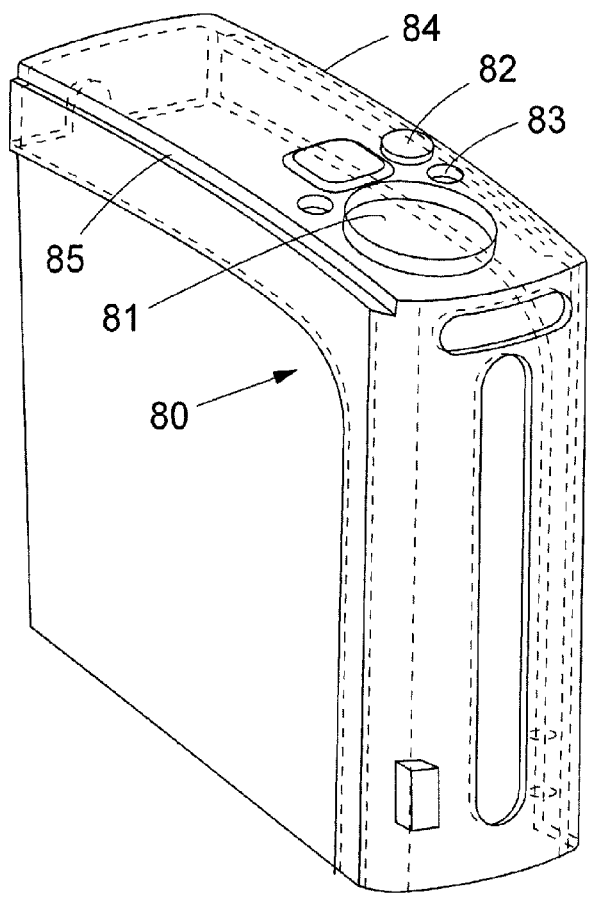
FIG. 3 is an elevated perspective view of the anesthetic vaporizer of FIG. 2 with a lid shown in FIG. 4 removed, revealing a refill port.

FIG. 3 is a perspective view of a part 80 of the anesthetic vaporizer 100 equipment comprising an opening 81 forming the port 18. Moreover, there is provided a recess 82 for enclosing the sensor 74 and a hole 83 for an attachment screw. Moreover, the part 80 comprises grooves 84, 85 forming seats for rails of the lid.

Figure 4:
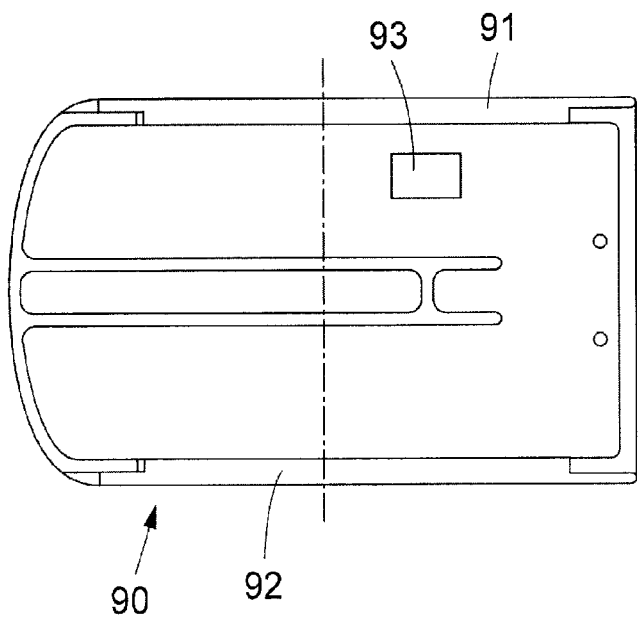
FIG. 4 is a bottom view of the lid comprised in the embodiment of FIG. 2.

FIG. 4 is a bottom view of the lid 90. The lid 90 is provided with rails 91, 92 mating with the grooves 84, 85 in the part 80. Moreover, a reflecting plate 93 is arranged at the bottom side of the lid 90.

Figure 5:
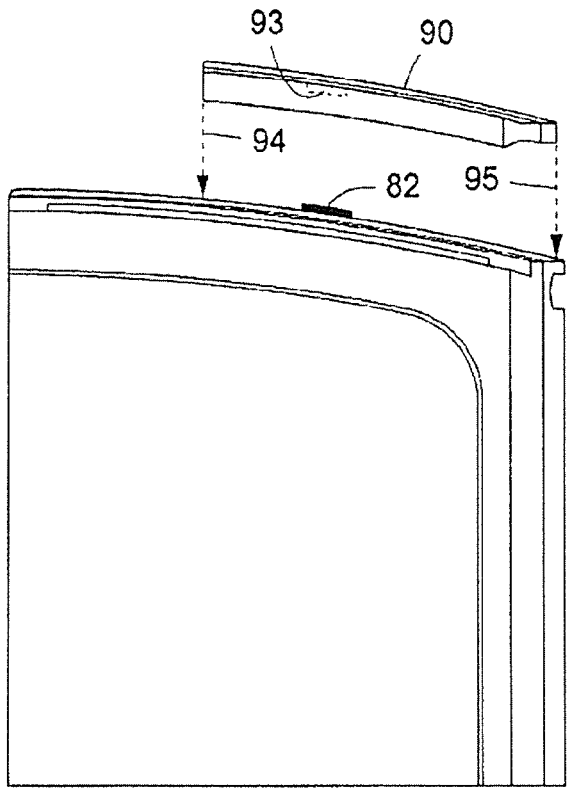
FIG. 5 is an exploded side view of the an anesthetic vaporizer of FIG. 2 and the lid of FIG. 4.

FIG. 5 is a side view of the part 80 with the lid 90 lifted up. In a home position, the lid is arranged as shown by arrows 94, 95, so that the lid 90 covers the opening 81. Thus, dust and debris cannot enter the port 18 during normal use. Moreover, the port 18 is not accessible by mistake. Thus, the port is protected from unintended operation of the valve system therein.

In the home position, the reflecting plate 93 is positioned opposite the opening 82, which houses the sensor 74. Thus, the sensor 74 emits a signal when the lid is in its home position, at least covering the port 18.

When the anesthetic vaporizer is to be refilled with liquid anesthetic agent, the lid is pushed aside to the left in FIG. 5 and a bottle containing anesthetic agent is inserted into the opening 81. Then, the reflecting plate 93 will no longer be positioned opposite the sensor 74 and the sensor will no longer emit a signal. The ceasing of the signal will influence upon the control device to perform actions, for example as indicated above.

Figure 6:
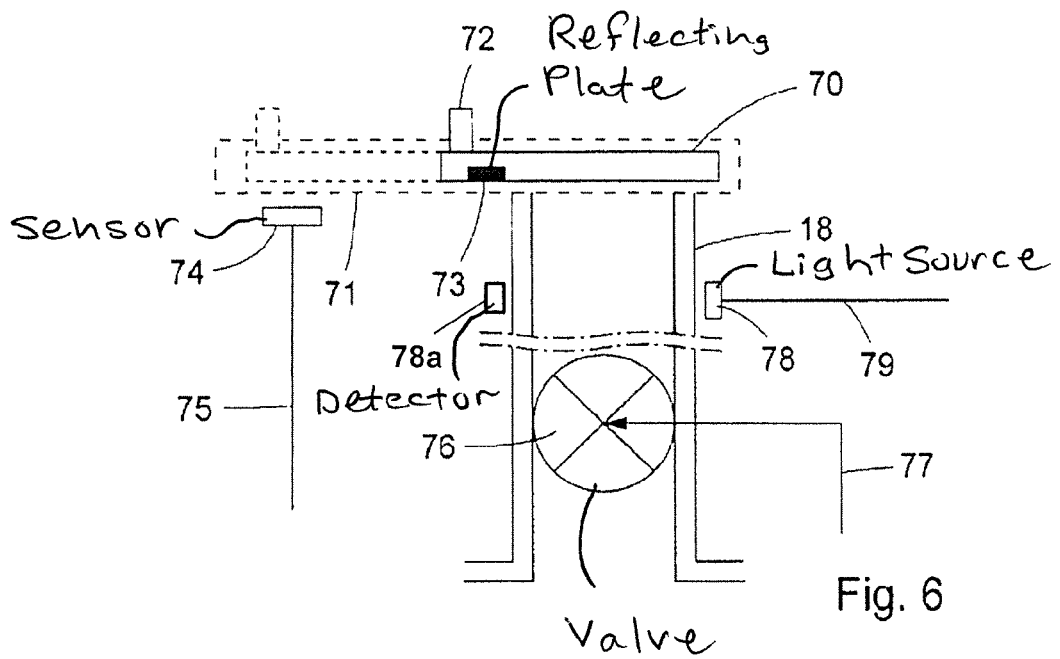
FIG. 6 is a schematic block diagram of another comprising an embodiment of the invention.

In a further embodiment, the breathing apparatus for delivery of an anesthetic agent having an anesthetic agent vaporizer may also in addition or alternatively include a second sensor, see FIG. 6, which detects when a filling vessel is inserted in the port 18. The second sensor emits a signal on a line 79. The sensor may be an optical sensor that comprises a light source 78, such as a LED, arranged at one side of the port 18 and a detector 78a arranged at the other side of the port. Thus, the second sensor normally emits a signal on line 79. When a refill adapter is inserted in the port 18, the light ray is broken and the signal from the second sensor ceases on line 79. Line 79 may be connected to the control device mentioned above.

Figure 7:
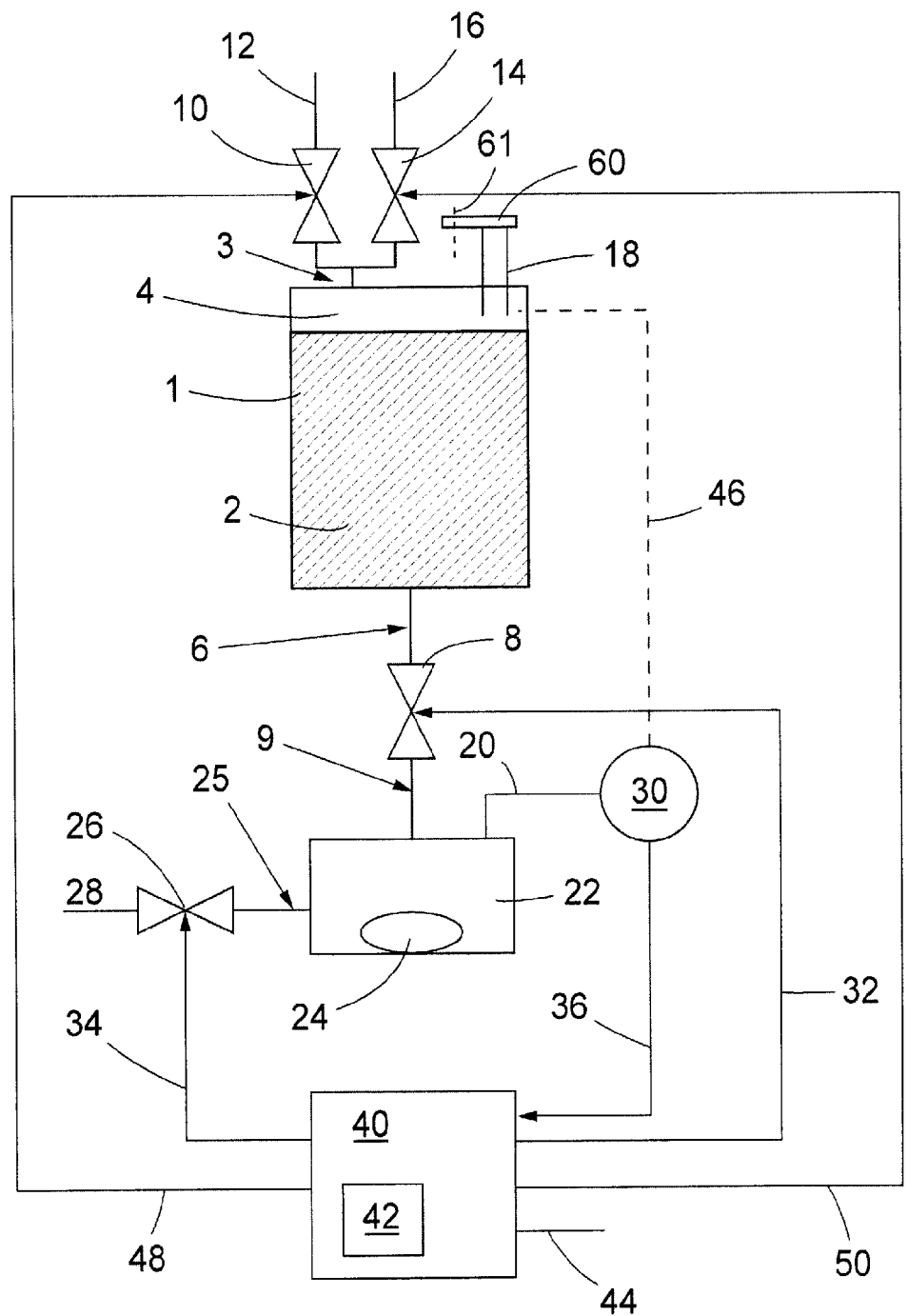
FIG. 7 is a schematic block diagram of another anesthetic vaporizer in an embodiment of the invention.

FIG. 7 schematically shows an anesthetic agent vaporizer comprising an embodiment of the present invention. The equipment comprises a primary reservoir 1 containing a medical liquid 2, such as an anesthetic agent, to be delivered to a patient, for example in a breathing gas stream. The space 4 above the medical liquid level is via a port 3 connected to a source for gas under pressure via a line 12 and a controllable first valve 10. The space 4 can also be connected to atmospheric pressure by a controllable second valve 14 and a line 16. The line 16 can be connected to a means for taking care of the gas expelled from the space 4, for example for reuse or for making the gas harmless. The other embodiments may have similar arrangements.

In contrast to the above described embodiments, an outlet 6 from the first reservoir 1 is via a controllable third valve 8 and a line 9 connected to a secondary reservoir 22. An outlet 25 from the secondary reservoir is via a controllable fourth valve 26 and a line 28 connected to a medical liquid consuming device. A pressure-maintaining member 24 is arranged inside the secondary vessel. The purpose of the secondary reservoir 22 is to provide uninterrupted delivery of an anesthetic agent during replenishment of the first reservoir 1.

The pressure inside the secondary reservoir 22 is measured by a sensor 30 via a line 20. The sensor may also measure the pressure in space 4 via a line 46 shown in broken lines. The pressure signal from the sensor 30 is sent via lines 36 to a control device 40 having a calculating unit 42. The control device 40 controls the four valves 10, 14, 8 and 26 via lines 48, 50, 32 and 34, respectively. The valves 10, 14, 8 and 26 are controlled by an algorithm processed in the calculating unit 42. The control device 40 may emit signals at a line 44, such as alarm signals at error conditions.

The operation of the secondary reservoir 22 and the control device 40 is not the object of the present invention and will not be further described, but reference is made to WO 2007/006348 of the same applicant as the present invention, the technical contents of which is incorporated in its entirety in the present specification by reference.

The primary reservoir 1 is provided with a refill port 18, which may be of the type disclosed in WO 2005/056093.

In order to protect the port 18 from being contaminated by dust and debris during use, the port 18 is normally closed by a protecting member 60 according to the embodiment shown in FIG. 7. Such a protecting member can be of any suitable type, for example a screw cap for closing the port 18 in a gas-tight manner. The protecting member may be a wall closing the entrance to the port 18 without sealing it in a gas-tight manner. The protecting member also prevents unintended operation of the port and the valve system in the port. The protecting member 60 is removable or displaceable in order to expose the port 18. It may be rotatable around a shaft 61 as indicated by a broken line in FIG. 1.

Alternatively or additionally, the protecting member may be linearly displaceable as shown in FIG. 6, which discloses the port 18 provided with a lid 70. The lid 70 is arranged in a groove 71 of the anesthetic vaporizer. The lid 70 is, by means of a handle 72, moveable between a first position, shown in solid lines and closing the entrance of port 18, and a second position shown in broken lines and exposing the opening 18 so that a bottle can be inserted in the port.

The lid 70 is provided with an indication in the form of a reflecting plate 73 arranged below the handle 72. In this embodiment, sensor 74 is arranged in a position opposite to the reflecting plate 73 when the lid is in its opened position, as shown in FIG. 6 by broken lines.

When the reflecting plate 73 is moved to be positioned opposite to the sensor 74, the light from the light source, such as a light emitting diode LED, is reflected by the reflecting plate 73 towards the detector, which generates an output signal on a line 75. The line 75 may be connected to the control device 40 in the embodiment of FIG. 1, or may be connected to a separate control circuit.

If the line 75 is connected to the control device 40, the control device 40 may have a control program, which upon receipt of a signal from the sensor 74 performs one or several of the following operations:

1) valve 8 is closed via line 32 in order to isolate the secondary reservoir 22 from the first reservoir 1; and 2) valve 10 is closed via line 48 and valve 14 is opened via line 50 in order to reduce the pressure in the space 4 to atmospheric pressure.

When the bottle is removed and the lid 70 is returned to its closed position, the signal on line 75 disappears. Then, the control device 40 can be arranged to reverse the above-mentioned operations of the valves, in order to place the equipment in an operating condition, after being refilled.

As an extra safety measure, the port 18 may be provided with a fifth valve 76 controllable via a line 77. The control device 40 may be arranged to open the fifth valve 76 to allow medical liquid from a connected bottle to enter the primary reservoir and gas to enter the bottle from the reservoir replacing the liquid. In this way, the valve 76 is opened when the pressure in the space 4 is close to the atmospheric pressure, as sensed by the pressure sensor 30 via line 46.

Hence, refilling of the primary reservoir is effectively prevented when the latter is pressurized. Spillage of medical liquid is effectively prevented and safety of the device is increased.

The fifth valve 76 may be a pressure-controlled valve, which is closed when the pressure over the valve, and thus, the absolute pressure in the space 4, is above a predetermined value. When the pressure in space 4 is reduced by opening the second valve 14, the fifth valve 76 will automatically open, when the pressure is reduced below the predetermined pressure.

When the anesthetic vaporizer is to be refilled with anesthetic agent, the lid 70 is pushed aside to the left in FIG. 6 and a bottle containing anesthetic agent is inserted into the opening 81. Then, the reflecting plate 73 will be positioned opposite the sensor 74 and the sensor will emit a signal. The signal will influence upon the control device 40 to perform actions, for example as indicated above, such as closing the first valve 10 and third valve 8 followed by opening the second valve 14 in order to relieve pressure from chamber 1 and thus enable safe refilling of the reservoir 1 through the opening 81 and the port 18.

In addition, the control device 40 may be arranged to start a timer when the signal from the sensor 74 ceases. If the signal from the sensor 74 is not present again before a predetermined time period, the control device 40 may emit a warning signal. This may be desired if a user leaves a refill bottle for too long time in the port 18, which might be the case due to the human factor. The user may for instance be distracted by an emergency clinical situation during refill and leave the refill container unattended. The control device may be arranged to emit a warning signal in such cases.

Alternatively or additionally to emitting a warning signal, the control device 40 may be arranged, after the predetermined time period has elapsed, to close the fourth valve 76 to disconnect the bottle from the primary reservoir, close the second valve 16 and open the first valve 10 to pressurize the primary reservoir and finally open the third valve 8 in order to automatically restore normal operation of the anesthetic vaporizer. In order to refill the primary reservoir again, the bottle has to be removed and the lid 70 closed to the home position, whereupon a new filling procedure may take place.

The anesthetic vaporizer can also include a second sensor 78, see FIG. 6, which detects when a refilling vessel is inserted in the port 18, as explained above. The second sensor emits a signal on line 79. In addition to the above described arrangement of the second sensor 78, or alternatively, for instance an adapter or neck of a refill vessel may comprise a sensor detectable unit, such as a reflecting part detectable by an optical sensor, a magnet detectable by a Hall sensor, transponder returning a signal on a request signal, etc. The sensor detectable unit allows reliable detection thereof when inserted into port 18. Line 79 may be connected to the control device 40 or other control devices.

The anesthetic agent may be one of Halothane, Isoflurane, Sevoflurane, Enflurane, Desflurane, or other medical agents suitable for delivery an anesthetic vaporizer.

The refill condition may also be a filling condition, when filling for the first time. The filling action may be a refilling condition when replenishing the receptacle of an anesthetic vaporizer.

The sensors may be part of an anesthetic vaporizer itself or may be part of a breathing apparatus in which the anesthetic vaporizer is to be operated.

In the above-mentioned embodiments, the sensors comprise a light source and a light detector. However, each sensor may operate with other types of radiation, such as any type of electromagnetic radiation, such as ultraviolet or infrared light or microwaves. Alternatively, sound, ultrasound may be used. A magnet and a Hall-sensor, a magnetic diode, a magnetostrictive or magnetoresistive sensor, or a Reed contact would also be possible to use. As an alternative capacitive sensors may be used. Also, temperature based sensors may be used, e.g. a Peltier element, a temperature controlled resistor, or thermoelements may detect a defined temperature provided by a units such as a heat generating resistor, a Peltier element etc. Also, an oscillator, such as a radio frequency oscillator, may change its frequency in dependence of a filling action. Mechanical sensors may be based on strain detection, piezoelectric pressure detecting sensors or accelerometers detecting a change of position of an element of an anesthetic breathing apparatus indicating a filling action. Furthermore, combinations of such sensor principles may be implemented suitably.

Still alternatively, the sensor may be a mechanical sensor, such as an electric switch or a mechanical rod, or a pneumatic or hydraulic sensor. In this embodiment, the sensor may directly influence upon and actuate the respective valves 12, 16 and 8 (and valve 76 if present).

The protection member may be moveable in a linear, rotational or pivoting movement.

Figure 8:
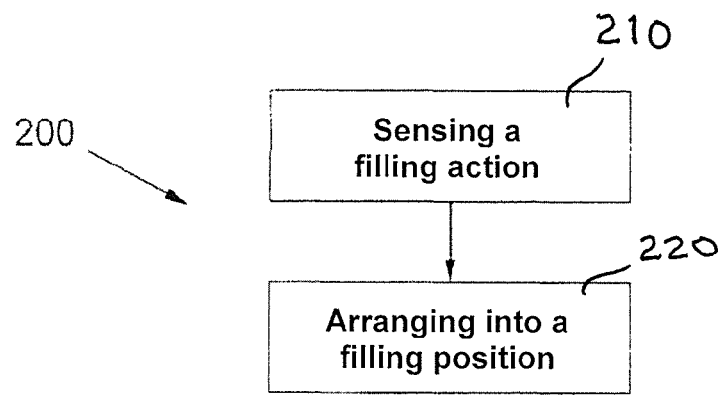
FIG. 8 is a flowchart illustrating a method according to an embodiment of the invention.

FIG. 8 is a flowchart illustrating a method according to an embodiment of the invention. A method of providing safety for an anesthetic vaporizer having a reservoir for containing a liquid anesthetic agent and a port for filling the reservoir with the liquid anesthetic agent, and a sensor device arranged adjacent the port. The method 200 includes sensing a filling action of the port with the sensor device in step 210. The method may include arranging the anesthetic vaporizer into a filling condition in step 220 upon sensing the filling action of the port.

Figure 9:
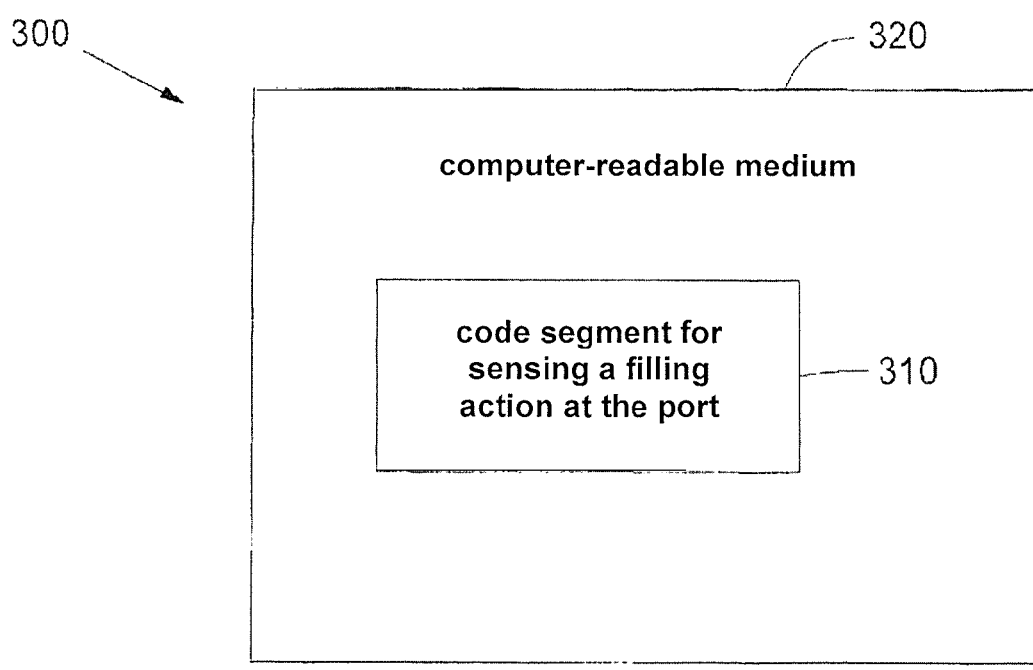
FIG. 9 is a schematic illustration of a computer program according to the invention.

FIG. 9 is a schematic illustration of a computer program according to the invention. A computer program 300 for providing safety for an anesthetic vaporizer is shown. The anesthetic vaporizer comprises a reservoir for containing a liquid anesthetic agent and a port for filling the reservoir with the liquid anesthetic agent, and a sensor device arranged adjacent the port. The computer program adapted for processing by a computer has a code segment 310 for sensing a filling action at the port with the sensor device. The computer program may enable carrying out of a method according to above with reference to FIG. 8. The computer program may be embodied on a computer-readable medium 320.

The invention can be implemented in any suitable form. The elements and components of the embodiments according to the invention may be physically, functionally, and logically implemented in any suitable way. Indeed, the functionality may be implemented in a single unit, in a plurality of units, or as part of other functional units.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

I claim as my invention:

1. A breathing apparatus comprising:
    a breathing circuit adapted to deliver inspiratory gas to, and receive expiratory gas from, a breathing subject;
    a reservoir containing a liquid anesthetic agent in an interior of said reservoir;
    an injector valve in fluid communication with said breathing circuit and with said interior of said reservoir;
    said reservoir comprising an inlet valve in fluid communication with said interior of said reservoir, above said liquid anesthetic agent in said interior of said reservoir;
    said reservoir comprising an outlet valve in fluid communication with said interior of said reservoir, above said liquid anesthetic agent in said interior of said reservoir;
    said reservoir comprising a normally closed refilling port at the reservoir that, when opened by a filling action, allows refilling of said reservoir with said liquid anesthetic agent;
    a control computer configured, while said refilling port is closed, to open said inlet valve to place said liquid anesthetic agent in said reservoir at an overpressure that is above atmospheric pressure, and to operate said injector valve to inject said liquid anesthetic agent, delivered to said injector valve by said overpressure, into said inspiratory gas;
    a filling action sensor at said port that detects an occurrence of said filling action and thereupon emits a filling action sensor signal; and
    said control computer being in communication with said filling action sensor to receive said filling action sensor signal therefrom, said control computer, upon receiving said filling actions sensor signal, being configured to automatically open said outlet valve to relieve said overpressure in said interior of said reservoir until atmospheric pressure is reached in said interior of said reservoir, and thereby automatically precluding said filling action from occurring while said overpressure exists in said interior of said reservoir.

2. The breathing apparatus of claim 1, wherein said port comprises further comprising a protection member that normally closes said port, and wherein said filling action sensor detects a displacement of said protection member.

3. The breathing apparatus of claim 2, wherein said protection member, when closing said port, is located in a home position, and wherein said filling action sensor detects displacement of said protection member from said home position.

4. The breathing apparatus of claim 3, wherein said filling action sensor is configured to emit said filling action sensor signal as long as said protection member is in said home position and to cease to emit said output signal when said protection member is displaced from said home position.

5. The breathing apparatus of claim 2, wherein said filling action sensor is configured to emit said filling action sensor signal when said protection member is located in a position that opens said refill port.

6. The breathing apparatus of claim 5, wherein said protection member is a lid that is movable to open said port by executing a movement selected from the group consisting of a linear movement, a rotational movement and a pivoting movement.

7. The breathing apparatus of claim 1, wherein said filling action sensor is configured to detect insertion of a filling vessel into said refill port.

8. The breathing apparatus of claim 7, wherein said filling action sensor comprises an emitter located at a side of said port that emits an emitter signal, and a detector located at an opposite side of said port that detects said emitter signal, and wherein said filling action sensor is configured to emit said filling action sensor signal when a filling vessel blocks said emitter signal from being detected by said detector.

9. The breathing apparatus of claim 7, wherein said filling action sensor comprises a detectable item carried by said filling vessel and a detector located at said refill port that detects said detectable item when said filling vessel is inserted into said refill port.

10. The breathing apparatus of claim 1, wherein said filling action sensor is configured to employ radiation selected from the group consisting of electromagnetic radiation, ultraviolet radiation, visible light radiation, and infrared radiation.

11. The breathing apparatus of claim 1, wherein said filling action sensor comprises a device selected from the group consisting of a mechanical sensor device, an electronic sensor device, a capacitive sensor device, a thermal sensor device, a magnetic sensor device, a pneumatic sensor device, a hydraulic sensor device, and combinations thereof.

12. The breathing apparatus of claim 1, wherein said control computer is configured to emit a warning signal when said filling condition or said filling action occurs for longer than a predetermined time duration.

13. The breathing apparatus of claim 1, wherein said control computer, upon receiving said filling action sensor signal, being configured to also at least partially interrupt operation of said injector valve.

14. The breathing apparatus of claim 13, wherein said control computer is configured to at least partially interrupt operation of said injector valve by interrupting delivery of said liquid anesthetic agent to said injector valve from said reservoir.

15. The breathing apparatus of claim 1 wherein said control computer, upon receiving said filling action sensor signal, is configured to also completely interrupt operation of said injector valve.

16. A method for operating a breathing apparatus comprising:
via a breathing circuit, delivering inspiratory gas to, and receiving expiratory gas from, a breathing subject;
containing a liquid anesthetic agent in an interior of a reservoir that comprises an inlet valve in fluid communication with said interior of said reservoir, above said liquid anesthetic agent in said interior of said reservoir, and an outlet valve in fluid communication with said interior of said reservoir, above said liquid anesthetic agent in said interior of said reservoir;
placing an injector valve in controlled fluid communication with said breathing circuit and with said interior of said reservoir;
allowing refilling of said reservoir via a normally closed refilling port at the reservoir that, when opened by a filling action, provides access to said interior of said reservoir for refilling of said reservoir with said liquid anesthetic agent;
from a control computer, while said refilling port is closed, opening said inlet valve to place said liquid anesthetic agent in said reservoir at an overpressure that is above atmospheric pressure, and operating said injector valve to inject said liquid anesthetic agent, delivered to said injector valve by said overpressure, into said inspiratory gas;
with a filling action sensor at said port, detecting an occurrence of said filling action and thereupon emitting a filling action sensor signal; and
providing said control computer with said filling action sensor signal and from said control computer, upon receiving said filling actions sensor signal, automatically open said outlet valve to relieve said overpressure in said interior of said reservoir until atmospheric pressure is reached in said interior of said reservoir, and thereby automatically precluding said filling action from occurring while said overpressure exists in said interior of said reservoir.

17. A non-transitory, computer-readable data storage medium encoded with programming instructions, said storage medium being loaded into a breathing apparatus comprising a breathing circuit adapted to deliver inspiratory gas to, and receive expiratory gas from, a breathing subject, a reservoir containing a liquid anesthetic agent in an interior of said reservoir, an injector valve in fluid communication with said breathing circuit and with said interior of said reservoir, said reservoir comprising an inlet valve in fluid communication with said interior of said reservoir, above said liquid anesthetic agent in said interior of said reservoir, said reservoir comprising an outlet valve in fluid communication with said interior of said reservoir, above said liquid anesthetic agent in said interior of said reservoir, said reservoir comprising a normally closed refilling port at the reservoir that, when opened by a filling action, allows refilling of said reservoir with said liquid anesthetic agent, said programming instructions causing said control computer to:
while said refilling port is closed, open said inlet valve to place said liquid anesthetic agent in said reservoir at an overpressure that is above atmospheric pressure, and operate said injector valve to inject said liquid anesthetic agent, delivered to said injector valve by said overpressure, into said inspiratory gas;

receive a filling action sensor signal from a filling action sensor at said port upon detection of an occurrence of said filling action; and upon receiving said filling actions sensor signal, automatically open said outlet valve to relieve said overpressure in said interior of said reservoir until atmospheric pressure is reached in said interior of said reservoir, and thereby automatically preclude said filling action from occurring while said overpressure exists in said interior of said reservoir.

\* \* \* \* \*